(12) United States Patent
Shyu et al.

(10) Patent No.: US 8,319,971 B2
(45) Date of Patent: Nov. 27, 2012

(54) SCATTERFIELD MICROSCOPICAL MEASURING METHOD AND APPARATUS

(75) Inventors: Deh-Ming Shyu, Miaoli County (TW); Sen-Yih Chou, Taipei (TW); Yi-Sha Ku, Hsinchu (TW)

(73) Assignee: Industrial Technology Research Institute, Hsin-Chu (TW)

( * ) Notice: Subject to any disclaimer, the term of this patent is extended or adjusted under 35 U.S.C. 154(b) by 373 days.

(21) Appl. No.: 12/187,057

(22) Filed: Aug. 6, 2008

(65) Prior Publication Data
US 2010/0007881 A1    Jan. 14, 2010

(30) Foreign Application Priority Data
Jul. 8, 2008    (TW) ................. 97125643 A (51) Int. Cl.
*G01N 21/55* (2006.01)
(52) U.S. Cl. ............... 356/445; 356/497; 356/237.1; 359/235; 359/386
(58) Field of Classification Search .......... 356/445, 356/497, 237.1; 250/492.1, 201.3; 355/67, 355/43, 77
See application file for complete search history.

(56) References Cited

U.S. PATENT DOCUMENTS

| | | | | |
|---|---|---|---|---|
| 5,166,751 | A * | 11/1992 | Massig | 356/511 |
| 5,479,252 | A * | 12/1995 | Worster et al. | 356/237.5 |
| 5,963,314 | A * | 10/1999 | Worster et al. | 356/237.2 |
| 6,594,090 | B2 * | 7/2003 | Kruschwitz et al. | 359/707 |
| 6,646,716 | B1 * | 11/2003 | Ramanujan et al. | 355/67 |
| 6,721,094 | B1 * | 4/2004 | Sinclair et al. | 359/386 |
| 7,061,623 | B2 | 6/2006 | Davidson | |
| 7,586,594 | B2 * | 9/2009 | Hamamatsu et al. | 356/237.1 |
| 2003/0030902 | A1 * | 2/2003 | Fukushima et al. | 359/388 |
| 2007/0247616 | A1 | 10/2007 | Hamamatsu et al. | |
| 2008/0007808 | A1 * | 1/2008 | Ogasawara et al. | 359/30 |
| 2009/0273791 | A1 * | 11/2009 | Rigneault et al. | 356/511 |

FOREIGN PATENT DOCUMENTS

| | | |
|---|---|---|
| JP | 2003167197 A | 6/2003 |
| WO | 2006104184 A1 | 10/2006 |

OTHER PUBLICATIONS

Intellectual Property Office, Ministry of Economic Affairs, R.O.C., "Office Action", Jun. 20, 2012, Taiwan.
Heather J. Patrick et al., Scatterfield microscopy using back focal plane imaging with an engineered illumination field, Proc. of SPIE, 2006, vol. 6152, 61520J.

* cited by examiner

*Primary Examiner* — Gregory J Toatley
*Assistant Examiner* — Isiaka Akanbi
(74) *Attorney, Agent, or Firm* — Morris Manning & Martin LLP; Tim Tingkang Xia, Esq.

(57) ABSTRACT

The present invention provides a scatterfield microscopical measuring method and apparatus, which combine scatterfield detecting technology into microscopical device so that the microscopical device is capable of measuring the sample whose dimension is under the limit of optical diffraction. The scatterfield microscopical measuring apparatus is capable of being controlled to focus uniform and collimated light beam on back focal plane of an objective lens disposed above the sample. By changing the position of the focus position on the back focal plane, it is capable of being adjusted to change the incident angle with respect to the sample.

14 Claims, 8 Drawing Sheets

SCATTERFIELD MICROSCOPICAL MEASURING METHOD AND APPARATUS

CROSS-REFERENCE TO RELATED PATENT APPLICATIONS

This application claims the benefit of Taiwan Patent Application Serial No. 097125643, filed Jul. 8, 2008, which status is pending, the disclosures for which are hereby incorporated herein in their entirety by reference.

FIELD OF THE INVENTION

The present invention relates to an optical measurement technology, and more particularly, to a scatterfield microscopical measuring method and apparatus capable of projecting a light beam at a variable projection angle onto an object.

BACKGROUND OF THE INVENTION

With rapid advance of manufacturing process, any advance process control (APC) designed for improving production yield must be able to perform a real-time in-situ analysis relating to parameter control while feeding back the analysis results to the APC for parameter adjustment. In the process of current semiconductor fabrication, feature size had been scaled down to 65 nm which is already smaller than optical diffraction limit. As it is noted that a projected feature size of 65 nm is beyond the resolution limit for any conventional microscope, the conventional microscopic imaging can no longer meet with the requirement of APC. Although both the scanning electron microscope (SEM) and atom force microscope (AFM) can provide sufficient resolution, they are not preferred since the electron beam of SEM will cause electric charge to accumulate on the specimen surface and thus cause the specimen to damage, not to mention that SEM can only inspect the surface structure of a specimen and lack the ability for internal inspection; and the AFM, being also incapable of internal inspection, is notoriously slow for most industrial inspection applications that it is not suitable to be used in any in-situ inspection.

It is known that the scatterfield microscopy is substantially a non-contact optical microscopy that not only it is capable of achieving a resolution beyond the diffraction limit, but also it can inspect a specimen of multi-layered structure by regression calculation in a speed fast enough for any in-situ inspection. Thus, scatterfield microscopy is becoming commonplace in many new-generation advance process control for semiconductor fabrication and inspection, and, there are already some semiconductor manufacturers who had applied scatterfield microscopy in their in-situ inspection processes.

Figure 1:
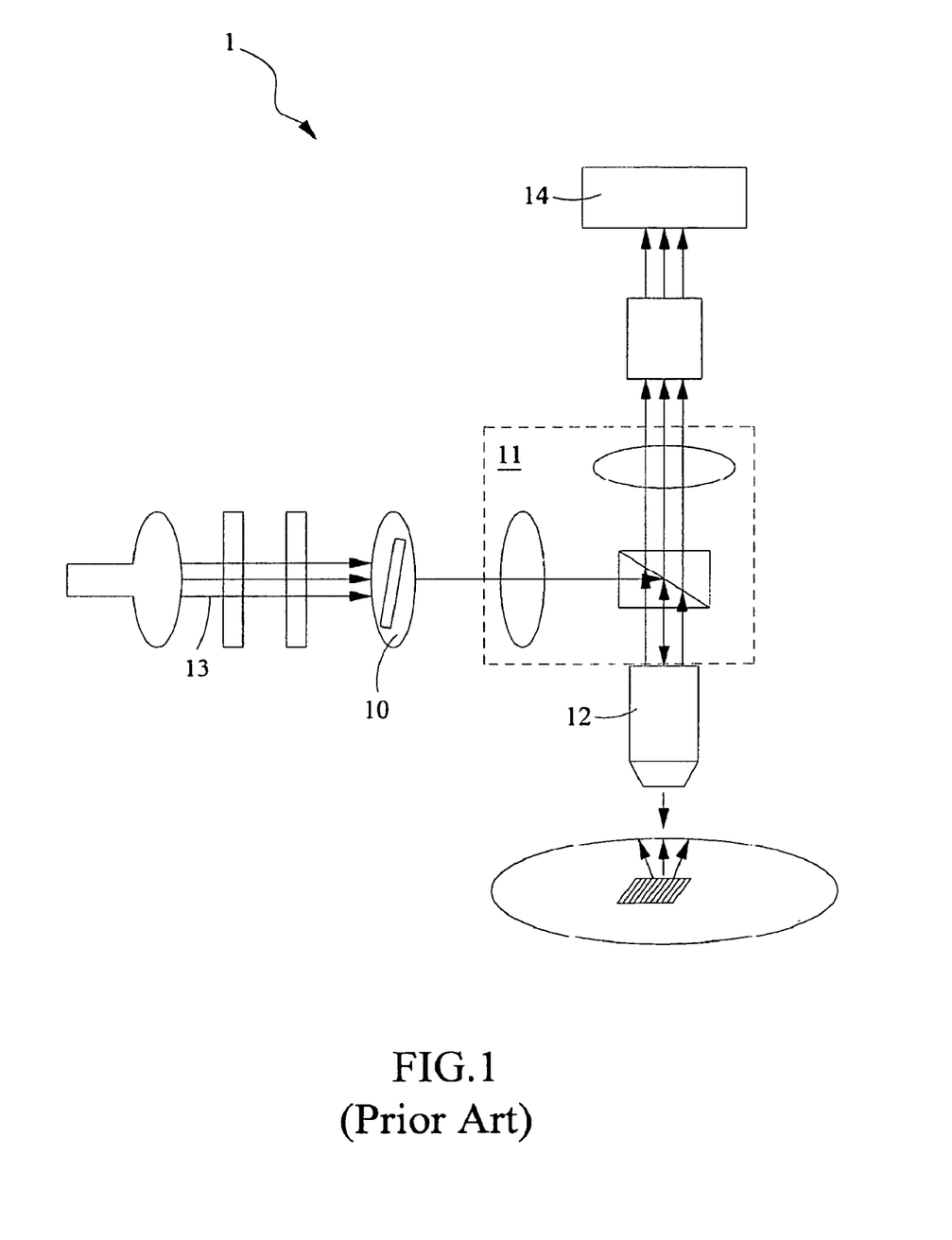
FIG. 1 is a bright-field reflection microscope disclosed in "Scatterfield microscopy using back focal plane imaging with an engineered illumination field", Proc. of SPIE, vol. 6152, 61520J(2006), by H. J. Patrick, R. Attota, B. m. Barnes, et al.

There are already many studies relating to the application of scatterfield microscopy. One of which is a microscopic system disclosed in "Scatterfield microscopy using back focal plane imaging with an engineered illumination field", Proc. of SPIE, vol. 6152, 61520J(2006), by H. J. Patrick, R. Attota, B. m. Barnes, et al. As shown in FIG. 1, the microscopic system 1 adopts a structure of bright-field reflection microscope with a mask 10, through with an image can be formed on the back focal plane of a objective lens 12 over the transmission of a relay unit 11. As the mask 11 is controlled to move by a control unit in a precise manner for changing the illumination angle of an incident beam 13 upon a sample accordingly, the imaging unit 14 is able to record scattering light of various angles.

Another such study is an inspection device disclosed in U.S. Pat. No. 7,061,623 B2, entitled "Interferometric back focal plane scatterometry with Koehler illumination". In an interference microscope used in the aforesaid U.S. patent, the positioning of a sample of that of a reference surface is controlled to move in a precise manner by a control unit, only the portion of an illumination light of specific characteristics is allowed to project on the sample while the other portion of the illumination light are blocked by destructive interference. Basically, the aforesaid patent use an interference spectroscopy for selecting incident beams of certain illumination angles to shine on the sample while using the same to register the reflection thereof.

SUMMARY OF THE INVENTION

The object of the present invention is to provide a scatterfield microscopical measuring method and apparatus, being structured and formed by integrating a scatterfield microscopic means with a bright-field microscopic device, by which a simple and stable mechanism of scatterfield microscopy is provided for enhancing the schedule convenience of an inspection process.

Another object of the invention is to provide a scatterfield microscopical measuring apparatus, being a simplified scatterometry capable of projecting a light beam at a variable projection angle onto a sample by the cooperation between a spatial light modulator with phase modulation ability and a immobile optical imaging device, that is structured as a simple and stable framework without the requirement of any precision position control since there is no moveable mechanism being configured therein and thus can be easily integrated with other processing modules.

To achieve the above objects, the present invention provides a scatterfield microscopical measuring apparatus, comprising: a light source module, for providing a light field; an objective lens module, being configured with a back focal plane and being disposed at a side of a sample to be inspected; a spatial light modulator, for modulating an optical characteristic of the light field to form a first beam focusing on the back focal plane while enabling the first beam to project on the sample where it is reflected back as a second beam focusing on the back focal plane; and a detector, for recording an optical image formed on the back focal plane in response to the second beam.

Moreover, in an exemplary embodiment, the present invention provides a scatterfield microscopical measuring method, comprising the steps of: providing a light field; modulating an optical characteristic of the light field for focusing the light field on a back focal plane of an objective lens module to form a first beam; projecting the first beam on a sample to be inspected where it is reflected and forms a second beam focusing on the back focal plane; recording an optical image formed on the back focal plane in response to the second beam; and performing an adjustment operation for changing the focusing position of the first beam on the back focal plane.

Further scope of applicability of the present application will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given herein below and the accompanying drawings which are given by way of illustration only, and thus are not limitative of the present invention and wherein.

DESCRIPTION OF THE EXEMPLARY EMBODIMENTS

For your esteemed members of reviewing committee to further understand and recognize the fulfilled functions and structural characteristics of the invention, several exemplary embodiments cooperating with detailed description are presented as the follows.

Figure 2:
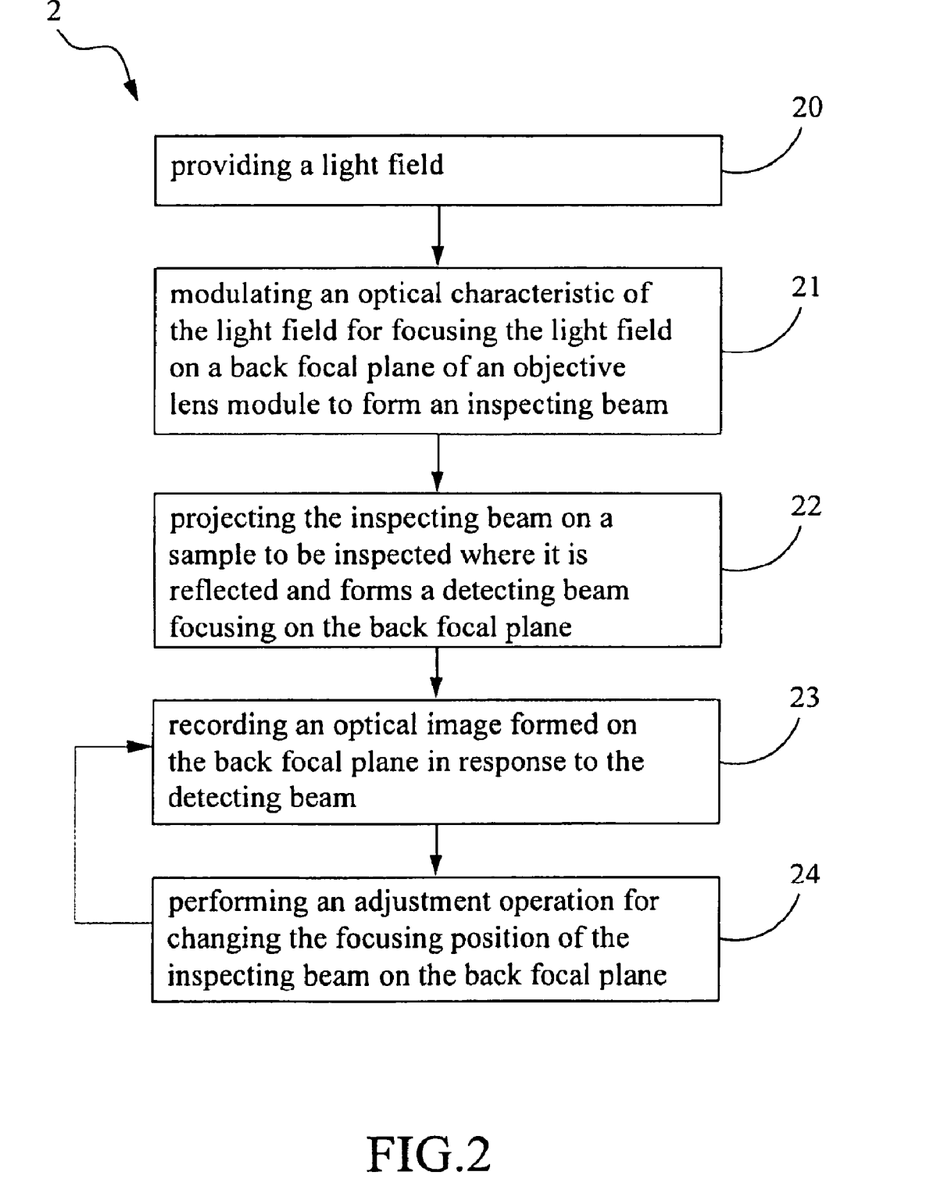
FIG. 2 is a flow chart depicting the steps of a scatterfield microscopical measuring method according to the present invention.

Please refer to FIG. 2, which is a flow chart depicting the steps of a scatterfield microscopical measuring method according to the present invention. The flow starts from step 20. At step 20, a light field is provided; and then the flow proceeds to step 21. It is noted that, in an exemplary embodiment, the light field can be collimated and polarized for transforming the same into a collimated and polarized light field. At step 21, an optical characteristic of the light field is selected to be modulated for focusing the light field on a back focal plane of an objective lens module to form a first beam, whereas the optical characteristic can be a characteristic selected from the amplitude of the light field, the phase of the light field and the combination thereof; and then the flow proceeds to step 22. At step 22, the first beam is projected on a sample where it is reflected and forms a second beam focusing on the back focal plane; and then the flow proceeds to step 23. At step 23, an optical image formed on the back focal plane in response to the second beam is recorded; and then the flow proceeds to step 24. At step 24, an adjustment operation is performed for changing the focusing position of the first beam on the back focal plane.

In the past few years, scatterometry has emerged as a method for performing line-width and line profile metrology, especially by the semiconductor industry. The method uses a periodic target containing repetitive lines whose profile, i.e., its width, height, and shape, is to be determined. The technique relies on the complicated behavior that the grating structure has on the diffracted light as a function of incident angle and wavelength, and the sensitivity to small changes in the grating profile. By comparing measurements with a library of calculated model results, the profile can be inferred. Thus, by the repetitive of the step 23 and step 24, a complete image relating a specific position of the sample that is formed on the back focal plane is recorded to be used for estimating parameters of the sample.

Figure 3:
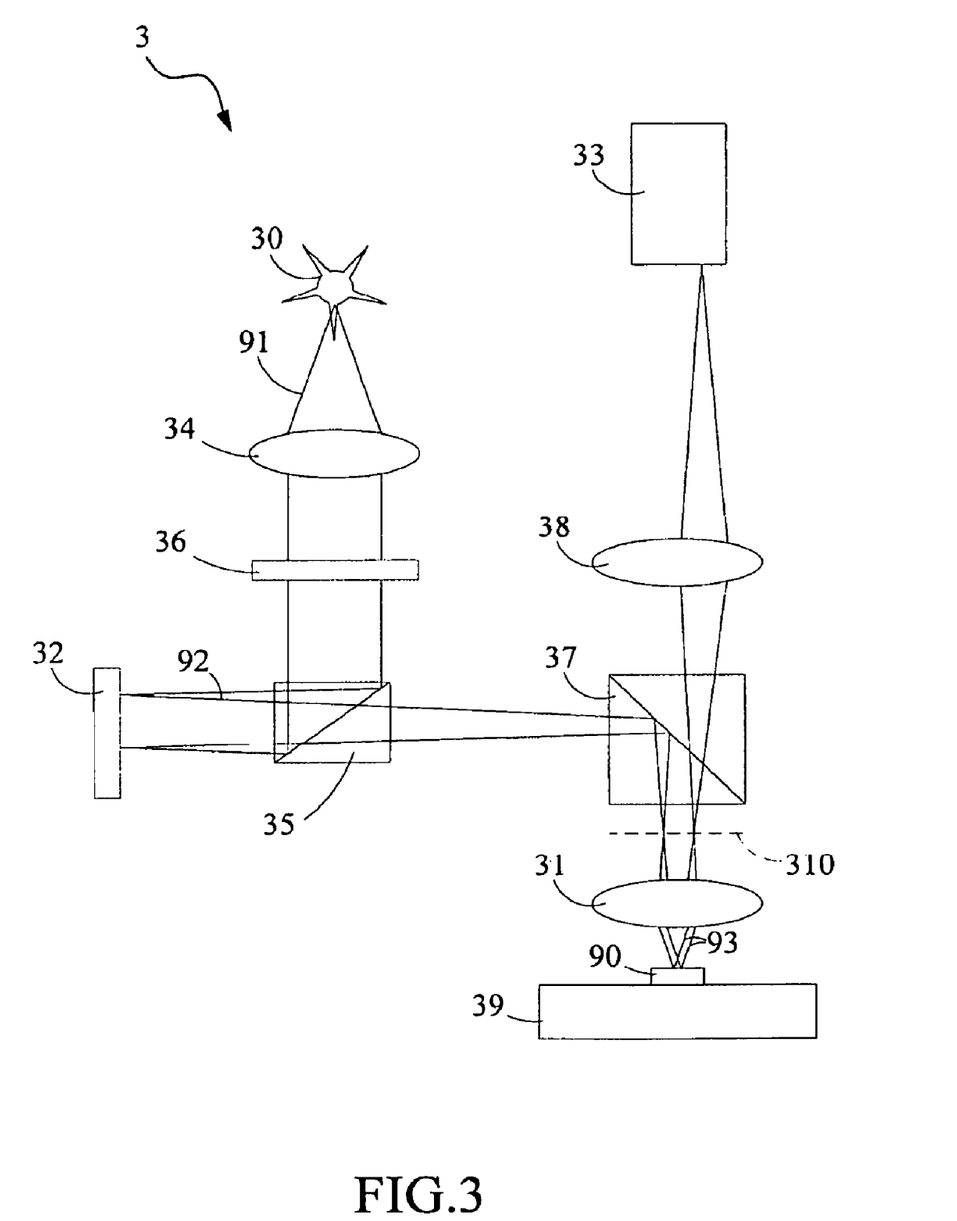
FIG. 3 is a schematic diagram showing a scatterfield microscopical measuring apparatus of the invention.

Please refer to FIG. 3, which is a schematic diagram showing a scatterfield microscopical measuring apparatus of the invention. The apparatus 3 comprises a light source module 30, an objective lens module 31, a spatial light modulator (SLM) 32, and a detector 33. The light source module 30 is used for providing a light field 91, which can be a laser module or a light-emitting diode (LED) module in this embodiment, but is not limited thereby. The objective lens module 31, which is configured with a back focal plane 310, is arranged at a side of a sample 90. The spatial light modulator 32 is used for modulating an optical characteristic of the light field 91 to form a first beam 92 focusing on the back focal plane 310 while enabling the first beam 92 to project on the sample 90 where it is reflected back as a second beam 93 focusing on the back focal plane 310. In this embodiment, the spatial light modulator 32 can be a liquid crystal modulator, such as the LC-R liquid crystal modulators from HOLOEYE Corp.

In the embodiment shown in FIG. 3, there are a lens set 34 and a first beam splitter 35 being arranged at positions between the light source module 30 and the spatial light modulator 32, in which the lens set 34 is used for collimating the light field 91 and the first beam splitter 35 is used for splitting the collimated light field while guiding the split light to the spatial light modulator 32. In addition, there is further a polarizer 36 being disposed at a position between the lens set 34 and the first beam splitter 35 that is used for polarizing the collimated light field. It is noted that the polarizer 36 can be a linear polarizer. Moreover, the detector 33 is used for recording an optical image formed on the back focal plane 310 in response to the second beam 93, so that the detector 33 can be a charge couple device (CCD) or a complementary metal-oxide-semiconductor (CMOS) device. In FIG. 3, there is further a second beam splitter 37 and another lens set 38 being arranged at positions between the detector 33 and the objective lens module 31, in which the second beam splitter 37 is used for guiding the first beam 92 to the back focal plane 310; and the lens set 38 is used for focusing the second beam 93 on the detector 33 after it is scattered by the back focal plane 310.

Figure 4:
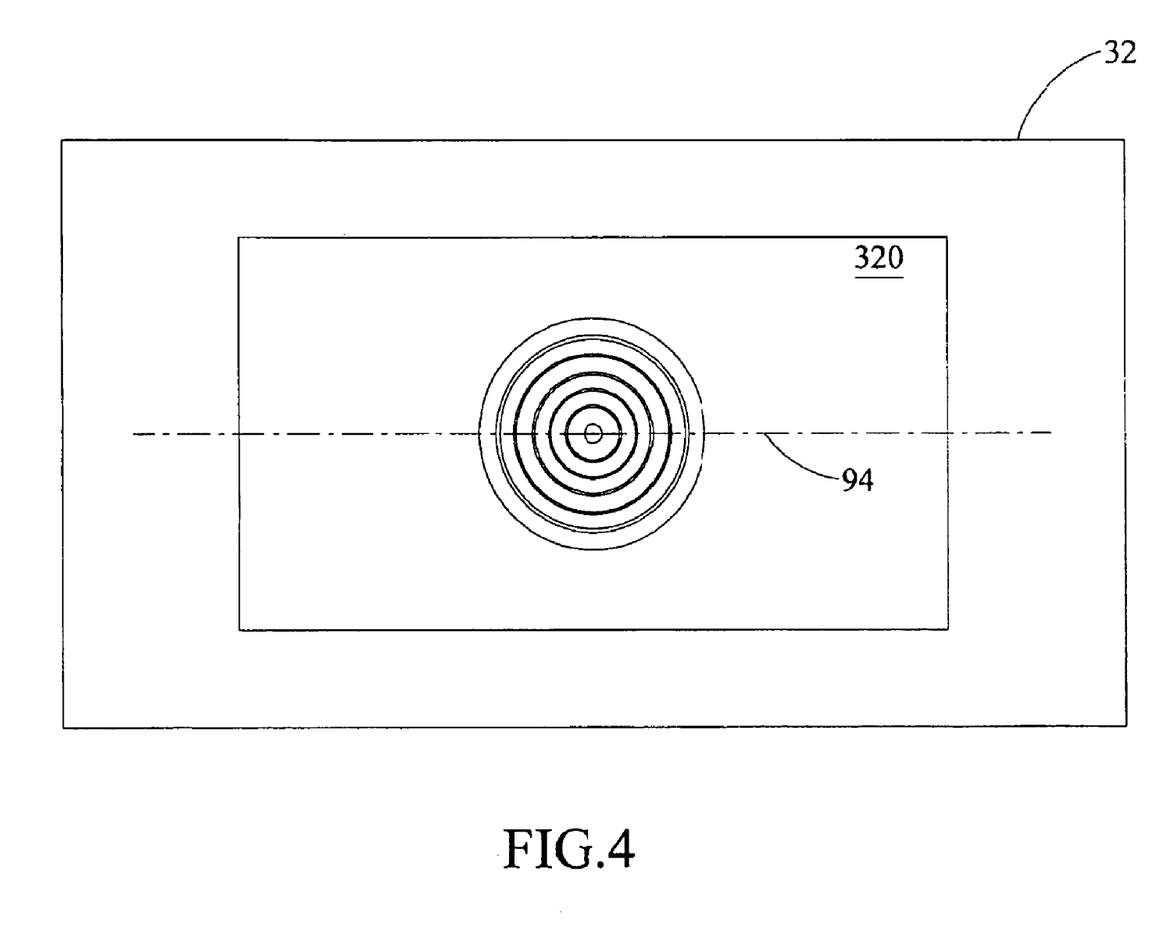
FIG. 4 is a schematic diagram showing a spatial light modulator.
Figure 5:
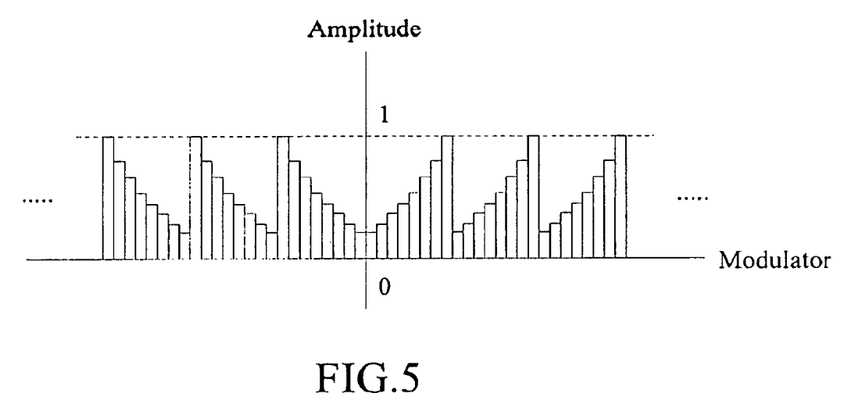
FIG. 5 is a schematic diagram depicting the amplitude modulation of a spatial light modulator.

Please refer to FIG. 4, which is a schematic diagram showing a spatial light modulator. As shown in FIG. 4, the working zone 320 of the spatial light modulator 32 is the composition of a plurality of modulation cells, that it is able to function like a Fresnel lens by amplitude modulation, phase modulation or the combination of the two. Please refer to FIG. 5, which is a schematic diagram depicting the amplitude modulation of a spatial light modulator. In FIG. 5, as the horizontal axis represents the locations on the spatial light modulator 32 which can be the center line 94 shown in FIG. 4; and the vertical axis represents the amplitude, the situation when the amplitude is 0 represents that no light is allowed to pass while the situation when the amplitude is 1 represents that all the light is allowed to pass. Thus, by controlling the light transmittance of each modulation cell, the spatial light modulator is able to act as a Fresnel lens and thus focus the incident light on the back focal plane 310 of the objective lens module 31.

Figure 7A:
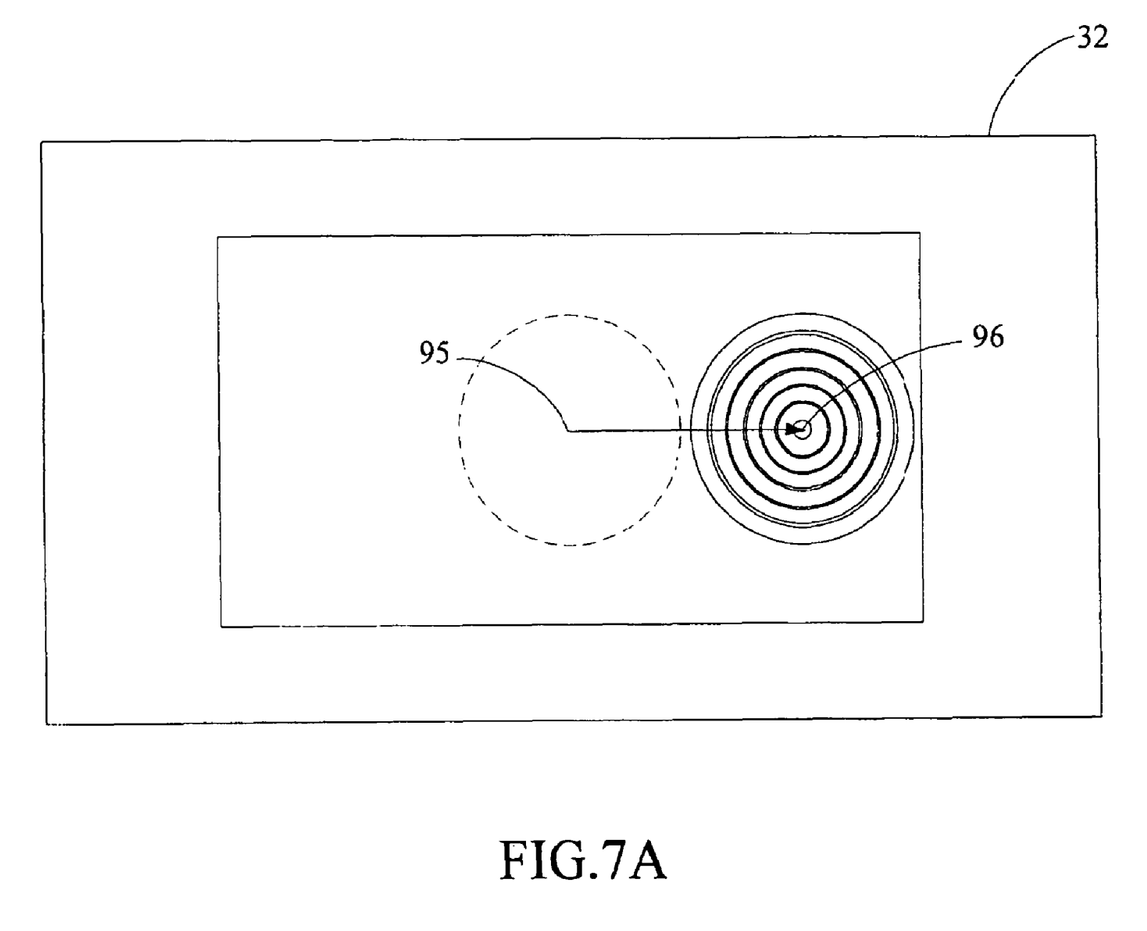
FIG. 7A and FIG. 7B are schematic diagrams showing how the changing of the center of a simulated Fresnel lens in a spatial light modulator is going to affect the first beam with respect to its focusing position.
Figure 7B:
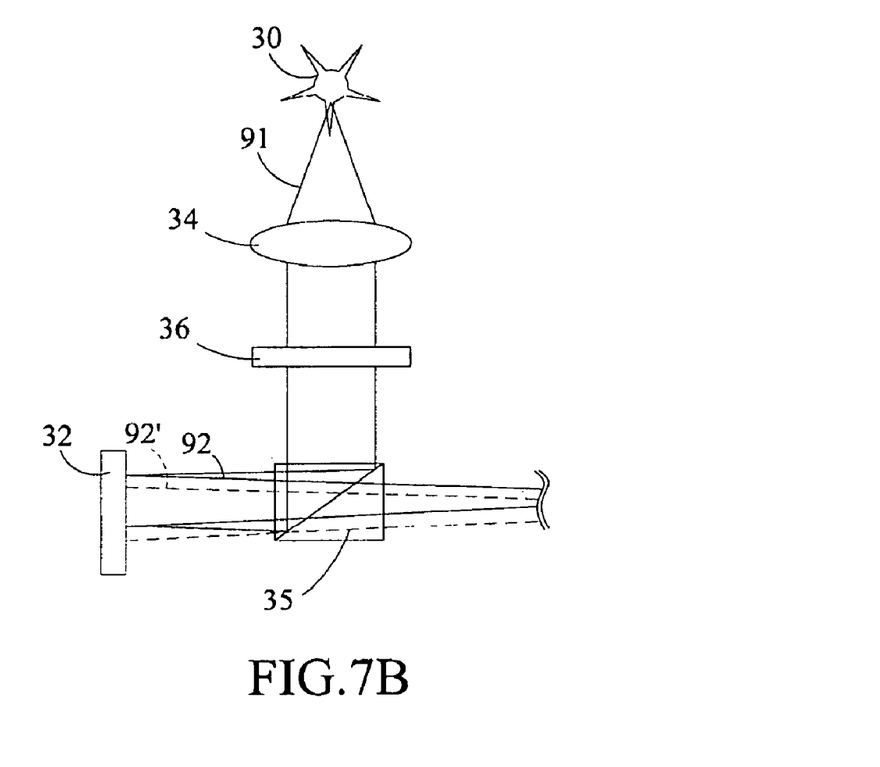
Figure 8:
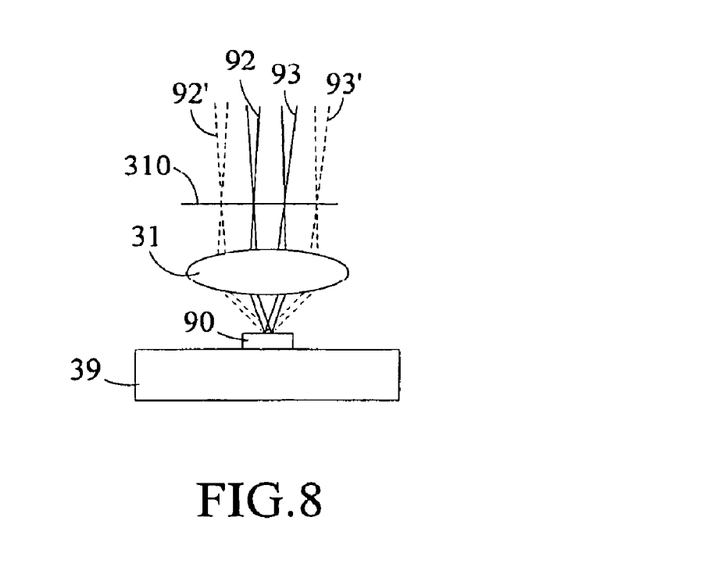
FIG. 8 is a schematic diagram showing how the changing of the focusing position of the first beam on the back focal plane is to affect the changing of the illumination angle of an incident beam upon a sample.

Please refer to FIG. 7A and FIG. 7B, which are schematic diagrams showing how the changing of the center of a simulated Fresnel lens in a spatial light modulator is going to affect the first beam with respect to its focusing position. As shown in FIG. 7A and FIG. 7B, as soon as the detector 33 finishes recording the scatterfield pattern on the back focal plane 310 relating to the first beam 92 that is being scattered by the spatial light modulator 32 when its modulation center is located at the position 95, the modulation center of the spatial light modulator 32 will be changed so as to change the focusing position of the first beam on the back focal plane. In FIG. 7A, when the modulation center is moved from the position 95 to another position 96, it is noted that the center of the first beam is going to change accordingly. As shown in FIG. 7B, the first beam 92 is changed into another first beam 92' after being modulated, and thereby the focusing position of the first beam 92' on the back focal plane 310 is moved consequently so that the illumination angle of the first beam 92' upon the sample 90 will not be the same as that of the first beam 92. Please refer to FIG. 8, which is a schematic diagram showing how the changing of the focusing position of the first beam on the back focal plane is to affect the changing of the illumination angle of an incident beam upon a sample. In FIG. 8, the focusing position of the second beam 93' on the back focal plane 310 relating to the first beam 92' is not the same as that of the second beam 93 relating to the first beam 92. Therefore, it is noted that by the changing of the focusing position of the first beam on the back focal plane 310, the illumination angle of an incident beam upon a sample 90 is going to change accordingly.

Figure 6:
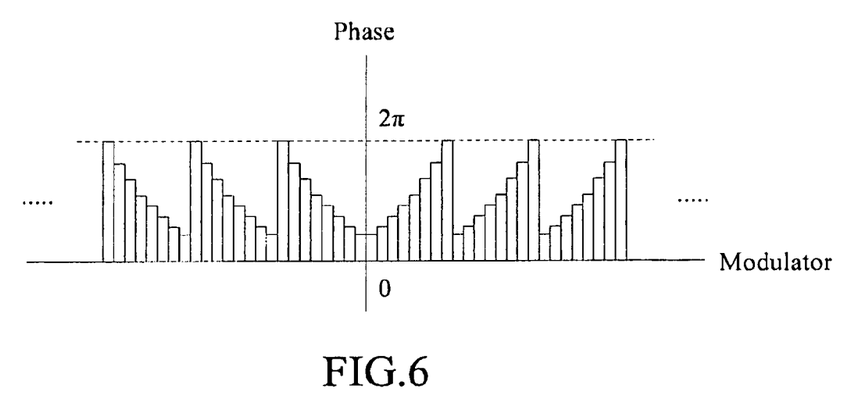
FIG. 6 is a schematic diagram depicting the phase modulation of a spatial light modulator.
Figure 9:
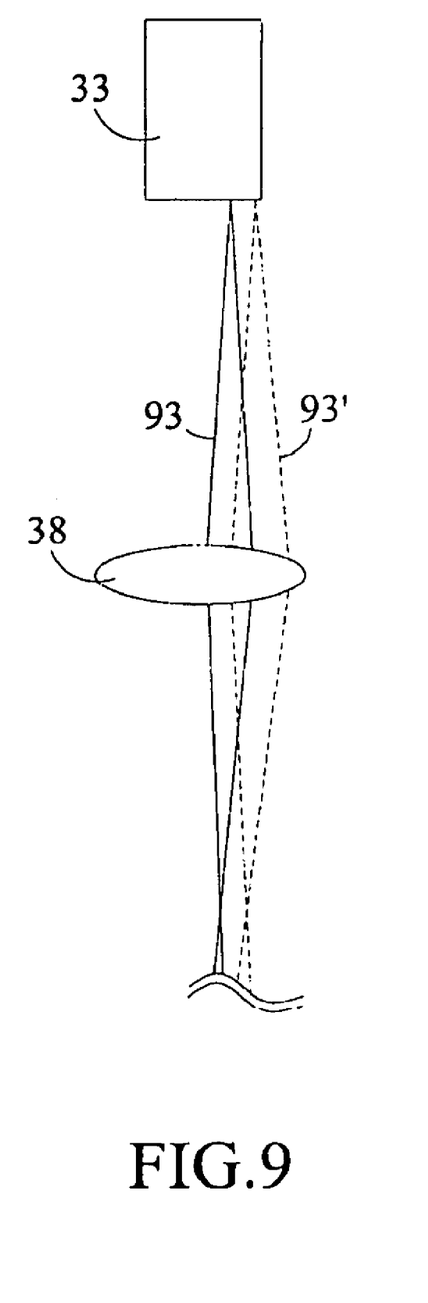
FIG. 9 is a schematic diagram showing how the changing of focusing position on the back focal plane is to affect the images captured by a detector.

Please refer to FIG. 6, which is a schematic diagram depicting the phase modulation of a spatial light modulator. In FIG. 6, the horizontal axis represents the locations on the spatial light modulator 32 which can be the center line 94 shown in FIG. 4; and the vertical axis represents the phase. By controlling the phase modulation of each modulation cell between 0 to 2 π, the spatial light modulator 32 is able to function as a Fresnel lens for controlling the first beam to focus on various positions on the back focal plane 310. Similar to that shown in FIG. 7A, simply by changing the modulation center of the spatial light modulator 32, the focusing position of the first beam on the back focal plane 310 can be changed accordingly. Furthermore, in FIG. 3, as all the second beams reflected from the sample 90 will be guided to project on the detector 33 by the lens set 38, the second beams 93, 93' resulting from different the illumination angles of the first beams 92, 92' upon the sample 90 will project on the detector 33 at different locations, as those shown in FIG. 9.

To sum up, the present invention provides a scatterfield microscopical measuring apparatus and method, being a simplified scatterometry capable of projecting a light beam at a variable projection angle onto a sample by the cooperation between a spatial light modulator with phase modulation ability and a immobile optical imaging device, that the apparatus is structured with a simple framework for enhancing the schedule convenience of an inspection process, and thus can be easily integrated with other processing modules.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

What is claimed is:

1. A scatterfield microscopical measuring apparatus, comprising:
    a light source module, for providing a light field;
    an objective lens module, being configured with a back focal plane and being disposed at a side of a sample to be inspected;
    a spatial light modulator, disposed on an optical path defined between the light source module and the sample, comprising a plurality of modulation cells, wherein by controlling the light transmittance of each modulation cell, the spatial light modulator is configured to act as a simulated Fresnel lens for modulating an optical characteristic of the light field provided from the light source module to form a first beam focusing on the back focal plane while enabling the first beam to project on the sample where it is reflected back as a second beam focusing on the back focal plane; and
    a detector, for recording an optical image formed on the back focal plane in response to the second beam,
    wherein a center of the simulated Fresnel lens in the spatial light modulator is changed so as to change the focusing position of the first beam on the back focal plane so that an illumination angle of the first beam upon the sample is going to change accordingly.

2. The apparatus of claim 1, wherein the spatial light modulator is a liquid crystal modulator.

3. The apparatus of claim 1, further comprising:
    a lens set, being disposed at a position between the light source module and the spatial light modulator to be used for collimating the light field; and
    a first beam splitter, being disposed at a position between the source module and the spatial light modulator to be used for splitting the collimated light field while guiding the split light to the spatial light modulator.

4. The apparatus of claim 3, further comprising:
    a polarizer, being disposed at a position between the lens set and the first beam splitter to be used for polarizing the light field.

5. The apparatus of claim 4, wherein the polarizer is a linear polarizer.

6. The apparatus of claim 1, further comprising:
    a second beam splitter, being disposed at a position between the detector and the objective lens module to be used for guiding the first beam to the back focal plane; and
    a lens set, being disposed at a position between the detector and the objective lens module to be used for focusing the second beam on the detector after it is scattered by the back focal plane.

7. The apparatus of claim 1, wherein the detector is a device selected from the group consisting a charge couple device (CCD) and a complementary metal-oxide-semiconductor (CMOS) device.

8. The apparatus of claim 1, wherein the optical characteristic of the light field is a characteristic selected from the amplitude of the light field, the phase of the light field and the combination thereof.

9. A scatterfield microscopical measuring method, comprising the steps of:
    providing a light field from a light source module and a spatial light modulator comprising a plurality of modulation cells, wherein the spatial light modulator is disposed on an optical path defined between the light source module and a sample to be inspected;
    controlling the light transmittance of each modulation cell so that the spatial light modulator is configured to act as a simulated Fresnel lens for modulating an optical characteristic of the light field for focusing the light field on a back focal plane of an objective lens module to form a first beam;

projecting the first beam on the sample to be inspected where it is reflected and forms a second beam focusing on the back focal plane;

recording an optical image formed on the back focal plane in response to the second beam; and performing an adjustment operation for changing the focusing position of the first beam on the back focal plane, wherein changing the focusing position of the first beam is performed by changing a center of the simulated Fresnel lens in the spatial light modulator so as to change the focusing position of the first beam on the back focal plane so that an illumination angle of the first beam upon the sample is going to change accordingly.

10. The method of claim 9, wherein the optical characteristic of the light field is a characteristic selected from the amplitude of the light field, the phase of the light field and the combination thereof.

11. The method of claim 9, further comprising the step of:
collimating and polarizing the light field before the modulating of the optical characteristic.

12. The method of claim 11, wherein the polarizing of the light field is a linear polarization process.

13. The method of claim 9, wherein the modulating of the optical characteristic is performed by the use of a spatial light modulator.

14. The method of claim 13, wherein the spatial light modulator is a liquid crystal modulator.

* * * * *